United States Patent
Corwin et al.

(10) Patent No.: US 10,534,134 B2
(45) Date of Patent: Jan. 14, 2020

(54) FLUID-FILLED HOLLOW OPTICAL FIBER CELL

(71) Applicant: Kansas State University Research Foundation, Manhattan, KS (US)

(72) Inventors: Kristan L. Corwin, Manhattan, KS (US); Chenchen Wang, Shanghai (CN); Ryan Luder, Overland Park, KS (US); Sajed Hosseini Zavareh, Manhattan, KS (US); Brian Washburn, Manhattan, KS (US)

(73) Assignee: Kansas State University Research Foundation, Manhattan, KS (US)

( * ) Notice: Subject to any disclaimer, the term of this patent is extended or adjusted under 35 U.S.C. 154(b) by 0 days.

(21) Appl. No.: 16/087,493

(22) PCT Filed: Mar. 21, 2017

(86) PCT No.: PCT/US2017/023361
§ 371 (c)(1),
(2) Date: Sep. 21, 2018

(87) PCT Pub. No.: WO2017/165381
PCT Pub. Date: Sep. 28, 2017

(65) Prior Publication Data
US 2019/0101698 A1 Apr. 4, 2019

Related U.S. Application Data

(60) Provisional application No. 62/311,223, filed on Mar. 21, 2016.

(51) Int. Cl.
*G02B 6/255* (2006.01)
*G01N 21/03* (2006.01)
(Continued)

(52) U.S. Cl.
CPC ....... *G02B 6/2551* (2013.01); *G01N 21/0303* (2013.01); *G01N 21/278* (2013.01); *G02B 6/02328* (2013.01); *G02B 6/262* (2013.01)

(58) Field of Classification Search
None
See application file for complete search history.

(56) References Cited

U.S. PATENT DOCUMENTS 3,377,448 A * 4/1968 Baumbach ........... H01H 37/761
337/401
5,410,626 A * 4/1995 Okuta .................. G02B 6/2835
385/39
(Continued)

FOREIGN PATENT DOCUMENTS

CN    202533604    11/2012
WO    2016004661    1/2016

OTHER PUBLICATIONS

The International Search Report and Written Opinion dated Jul. 24, 2017, in PCT/US17/23361 filed Mar. 21, 2017.
(Continued)

*Primary Examiner* — Tina M Wong
(74) *Attorney, Agent, or Firm* — Hovey Williams LLP (57) ABSTRACT

A fluid-filled hollow optical fiber cell broadly includes a hollow-core optical fiber and a fluid. The optical fiber presents first and second fiber ends and a longitudinal passageway that extends continuously between the fiber ends. The fluid occupies the passageway, with the fiber ends being closed to hermetically seal the fluid within the optical fiber. The first fiber end has a rounded closed shape formed by at least partly melting the first fiber end to form melted fiber material, with the fiber material being permitted to
(Continued)

solidify without splicing the first fiber end to another fiber so that the fiber material terminates the passageway at the first fiber end.

19 Claims, 6 Drawing Sheets

(51) Int. Cl.
    *G01N 21/27*     (2006.01)
    *G02B 6/02*     (2006.01)
    *G02B 6/26*     (2006.01)

(56) References Cited

U.S. PATENT DOCUMENTS

| | | |
|---|---|---|
| 6,196,730 B1 | 3/2001 | Hammar |
| 7,154,081 B1 | 12/2006 | Friedersdorf et al. |
| 7,272,956 B1* | 9/2007 | Anikitchev ............ G02B 6/2835 385/115 |
| 9,372,299 B1* | 6/2016 | Yi ............................ H01J 65/042 |
| 9,709,730 B2* | 7/2017 | Cai ............................ G01N 21/03 |
| 2004/0136670 A1* | 7/2004 | Abeeluck ................ G02B 6/032 385/125 |
| 2006/0093290 A1* | 5/2006 | Fishteyn .................. C03C 25/68 385/115 |
| 2006/0174659 A1* | 8/2006 | Ganz ................. C03B 37/01211 65/412 |
| 2008/0037939 A1* | 2/2008 | Xiao .................... G02B 6/02376 385/96 |
| 2009/0306637 A1* | 12/2009 | Esch ........................ A61B 18/24 606/15 |
| 2011/0097045 A1* | 4/2011 | Benabid ............. G02B 6/02328 385/95 |
| 2011/0176130 A1 | 7/2011 | Gu et al. |
| 2011/0267612 A1* | 11/2011 | Roberts .................. G02B 6/021 356/301 |
| 2013/0305928 A1* | 11/2013 | Kojima .............. B01D 53/0407 96/108 |
| 2017/0006998 A1* | 1/2017 | Liu .......................... A45D 34/04 |
| 2018/0275048 A1* | 9/2018 | Das ..................... G01N 21/3504 |
| 2019/0101698 A1* | 4/2019 | Corwin .............. G01N 21/0303 |

OTHER PUBLICATIONS

Wang, Chenchen, "Optical frequency references in acetylene-filled hollow-core optical fiber and photonic microcells," Kansas State University, 2015 <URL: https://krex.k-state.edu/dspace/bitstream/handle/2097/18831/ChenchenWang2015.pdf?sequence=5>.

* cited by examiner

FLUID-FILLED HOLLOW OPTICAL FIBER CELL

CROSS-REFERENCE TO RELATED APPLICATIONS

This application is the National Stage of International Patent Application No. PCT/US2017/023361 filed Mar. 21, 2017, which claims the benefit of U.S. Provisional Application Ser. No. 62/311,223, filed Mar. 21, 2016, entitled FLUID-FILLED PHOTONIC MICROCELL, each of which is hereby incorporated in its entirety by reference herein.

FEDERALLY SPONSORED RESEARCH OR DEVELOPMENT

This invention was made with government support under Grant # FA 9550-11-1-0096 from the Air Force Office of Scientific Research. The United States government has certain rights in the invention.

BACKGROUND

1. Field

The present invention relates generally to optical frequency reference cells. More preferably, embodiments of the present invention concern a fluid-filled hollow optical fiber cell with a hollow-core optical fiber mounted in a ferrule.

2. Discussion of Prior Art

It is known in the art to calibrate a laser source with a gas reference cell. Conventional glass vapor reference cells include a hermetically sealed container with windows that permit light to pass through the container and gas sealed within the container. As described in U.S. Pat. No. 8,079,763, it is also known to form a gas cell from a hollow-core photonic crystal fiber. In particular, each end of the photonic crystal fiber is spliced to a corresponding optical fiber to seal gas within the photonic crystal fiber. In another conventional reference cell embodiment, each end of a hollow fiber is secured in fluid communication with a vacuum chamber, with an optical beam positioned in free space coupling with the hollow fiber.

However, prior art gas reference cells have various deficiencies. For instance, conventional glass vapor reference cells are generally bulky and expensive to manufacture. The gas cell disclosed in the '763 patent is difficult to manufacture, particularly for relatively short lengths of hollow-core, photonic crystal fiber.

SUMMARY

The following brief summary is provided to indicate the nature of the subject matter disclosed herein. While certain aspects of the present invention are described below, the summary is not intended to limit the scope of the present invention.

Embodiments of the present invention provide a fluid-filled hollow optical fiber cell that does not suffer from the problems and limitations of the prior art reference cells set forth above.

A first aspect of the present invention concerns a fluid-filled hollow optical fiber cell that broadly includes a hollow-core optical fiber and a fluid. The optical fiber presents first and second fiber ends and a longitudinal passageway that extends continuously between the fiber ends. The fluid occupies the passageway, with the fiber ends being closed to hermetically seal the fluid within the optical fiber. The first fiber end has a closed shape formed at least partly by melting the first fiber end to form melted fiber material, with the fiber material being permitted to solidify without splicing the first fiber end to another fiber so that the fiber material terminates the passageway at the first fiber end.

A second aspect of the present invention concerns a method of making a fluid-filled hollow optical fiber cell that broadly includes the steps of introducing a fluid into the passageway of a hollow-core optical fiber; and hermetically sealing the hollow-core optical fiber by closing first and second fiber ends of the optical fiber to prevent the fluid in the passageway from flowing through the first and second fiber ends. The sealing step includes the steps of at least partly melting at least one of the fiber ends to form melted fiber material and permitting the melted fiber material to solidify without splicing the first fiber end to another fiber so that the fiber material terminates the passageway at the at least one fiber end.

This summary is provided to introduce a selection of concepts in a simplified form that are further described below in the detailed description. This summary is not intended to identify key features or essential features of the claimed subject matter, nor is it intended to be used to limit the scope of the claimed subject matter. Other aspects and advantages of the present invention will be apparent from the following detailed description of the embodiments and the accompanying drawing figures.

BRIEF DESCRIPTION OF THE DRAWING FIGURES

Preferred embodiments of the invention are described in detail below with reference to the attached drawing figures, wherein.

The drawing figures do not limit the present invention to the specific embodiments disclosed and described herein. The drawings are not necessarily to scale, emphasis instead being placed upon clearly illustrating the principles of the preferred embodiment.

DETAILED DESCRIPTION OF THE PREFERRED EMBODIMENTS

Figure 1:
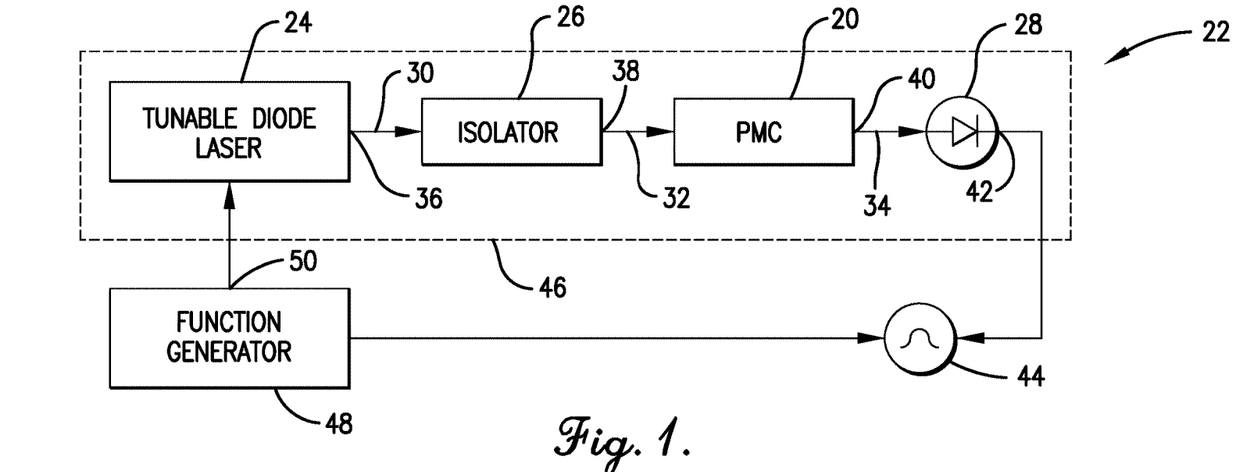
FIG. 1 is schematic view of a laser assembly constructed in accordance with a preferred embodiment of the present invention and including a tunable diode laser, an optical isolator, a photodetector, a function generator, an oscilloscope, and a fluid-filled hollow optical fiber cell.
Figure 2:
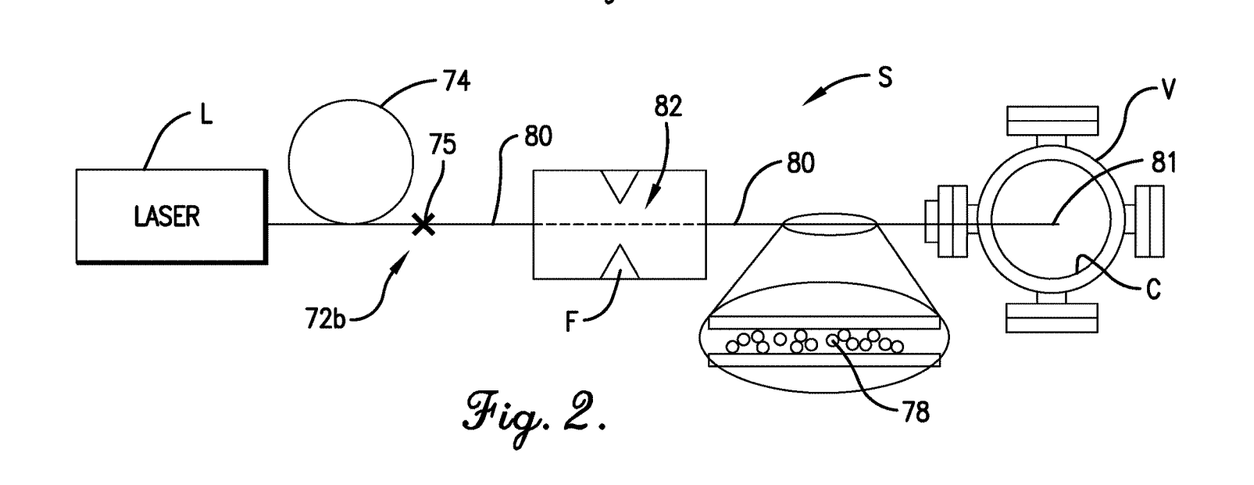
FIG. 2 is a schematic view of a fusion splicing system to produce the hollow optical fiber cell shown in FIG. 1, showing a laser, an electric arc fusion splicer, and a vacuum system V of the splicing system, with the splicing system depicted as receiving an intermediate fiber that includes a solid core fiber and an intermediate photonic crystal fiber joined at a splice to close an end of the intermediate photonic crystal fiber.
Figure 3:
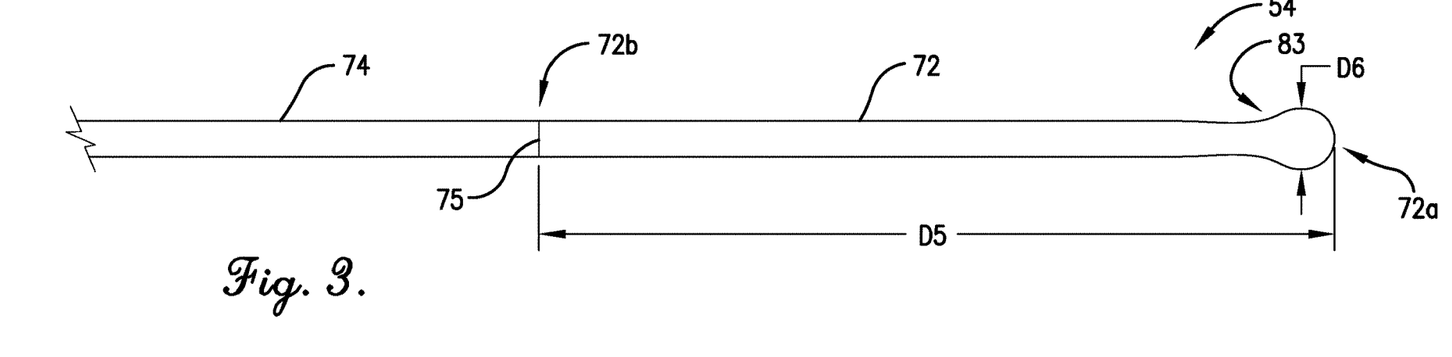
FIG. 3 is a fragmentary schematic view of the solid core fiber and the intermediate photonic crystal fiber shown in FIG. 2, but showing the intermediate fiber severed by a splicing process to form the rounded fiber end of the optical fiber assembly, with both ends of the photonic crystal fiber being closed to seal fluid within a passageway of the photonic crystal fiber.

Turning initially to FIGS. 1 and 2, a fluid-filled hollow optical fiber cell 20 (also referred to as an "HOFC") is constructed in accordance with a preferred embodiment of the present invention. As will be discussed further, the optical fiber cell 20 provides a very compact reference cell that can be used in various optical reference cell applications. In the illustrated embodiment, the optical fiber cell 20 is configured to be incorporated into a laser assembly 22 and used as a high-precision optical frequency reference for tunable laser calibration.

The laser assembly 22 is operable to provide a precisely-calibrated laser output. The laser assembly 22 preferably includes a tunable diode laser 24, an optical isolator 26, the optical fiber cell 20, a photodetector 28, and optical couplers 30,32,34.

The tunable diode laser 24 is conventional and provides an adjustable laser source. The isolator 26 is in optical communication with an output 36 of the laser 24 and, in the usual manner, prevents feedback of light to the laser 24. An output 38 of the isolator 26 is in optical communication with the optical fiber cell 20.

The optical coupler 34 comprises a multimode optical fiber. Preferably, the fiber of the optical coupler 34 presents a core diameter dimension (not shown) that ranges from about sixty-five microns (65 μm) to about four hundred microns (400 μm). More preferably, the core diameter dimension of the multimode optical fiber is about two hundred microns (200 μm).

The photodetector 28 is also conventional and converts an optical output 40 of the optical fiber cell 20 to an electrical signal. The photodetector 28 is in optical communication with the output 40 of the optical fiber cell 20. The photodetector 28 provides an output 42 that is in electrical communication with an oscilloscope 44.

In the illustrated embodiment, the laser 24, isolator 26, optical fiber cell 20, and photodetector 28 are preferably incorporated into a housing (not shown) to cooperatively provide a calibrating laser 46. However, one or more components of the calibrating laser 46 could be housed separately from the other components.

The laser assembly 22 also preferably includes the oscilloscope 44 and a function generator 48, both of which are conventional. An output 50 of the function generator 48 is provided to the laser 24. For instance, a ramp voltage can be provided by the function generator 48 to operate the laser 24 through a range of laser frequencies. Thus, in the usual manner, the electrical output 50 of the function generator 48 serves to control the output 36 of the laser 24.

The electrical output 50 of the function generator 48 is also provided to the oscilloscope 44. As a result, the oscilloscope 44 can be used to compare the voltage output 50 of the function generator 48 with the output 42 of the photodetector 28.

Again, the optical fiber cell 20 is configured to be incorporated into the laser assembly 22 as a high-precision frequency reference for tunable laser calibration. However, the optical fiber cell 20 could be used in other optical reference cell applications.

Turning to FIGS. 2-5, the optical fiber cell 20 comprises a compact, fluid-filled reference cell. The optical fiber cell 20 preferably includes a connector 52 and a fluid-filled optical fiber assembly 54 mounted in the connector 52 with cured epoxy 56 (see FIGS. 4 and 5).

Figure 4:
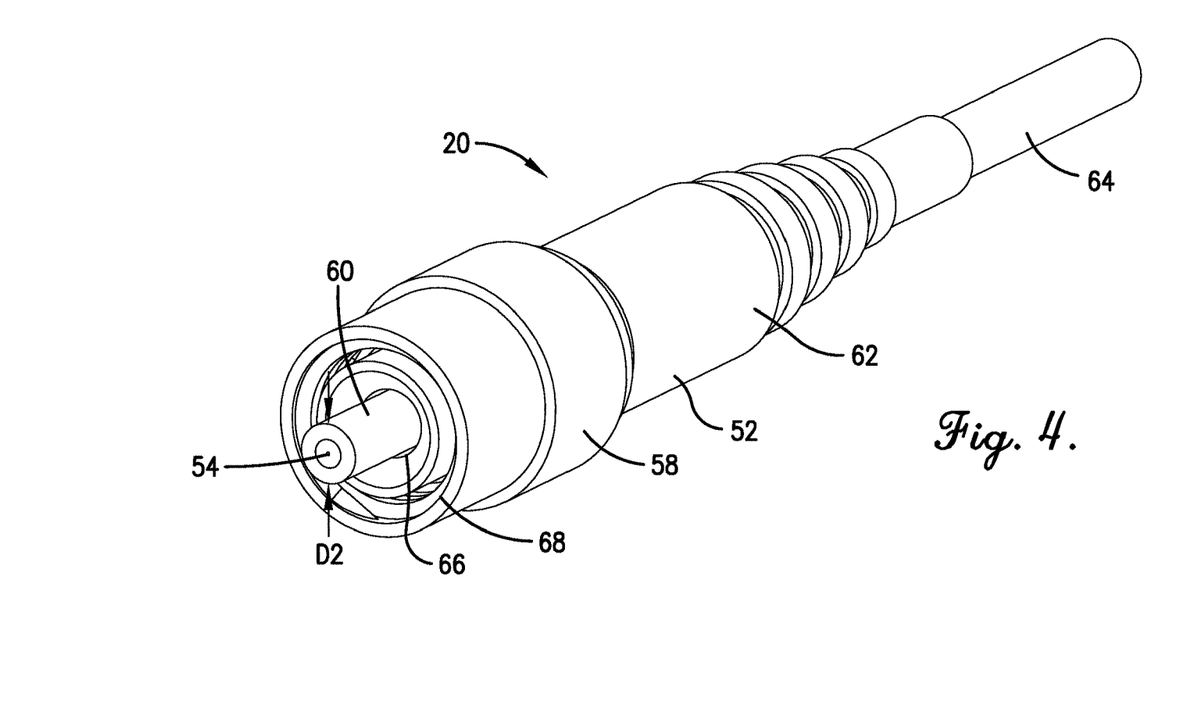
FIG. 4 is a fragmentary perspective view of the fluid-filled hollow optical fiber cell shown in FIG. 1, showing a connector and a fluid-filled optical fiber assembly of the optical fiber cell, with the connector including a connector housing, strain relief boot, and a ferrule, and with the optical fiber assembly secured within the connector.

The connector 52 preferably includes a connector housing 58, an optical ferrule 60, a strain relief boot 62, and a protective sleeve 64 (see FIG. 4). The connector housing 58 presents an opening 66 that receives the ferrule 60 and includes a threaded end 68 that surrounds the ferrule 60 (see FIG. 4). The connector 52 preferably comprises an FC/PC connector, although an alternative connector could be used without departing from the scope of the present invention.

In the illustrated embodiment, the protective sleeve 64 is partly received in the boot 62 so that the boot 62 and sleeve 64 both cover a splice in the optical fiber assembly 54. In this way, the boot 62 and sleeve 64 each provide a protective sleeve that covers and extends on opposite sides of the splice and thereby serves as a strain relief. However, the boot 62 and the sleeve 64 could be alternatively configured. For instance, where the splice is spaced outside of the boot 62, the sleeve 64 could be spaced from the boot 62 to cover the splice.

Figure 5:
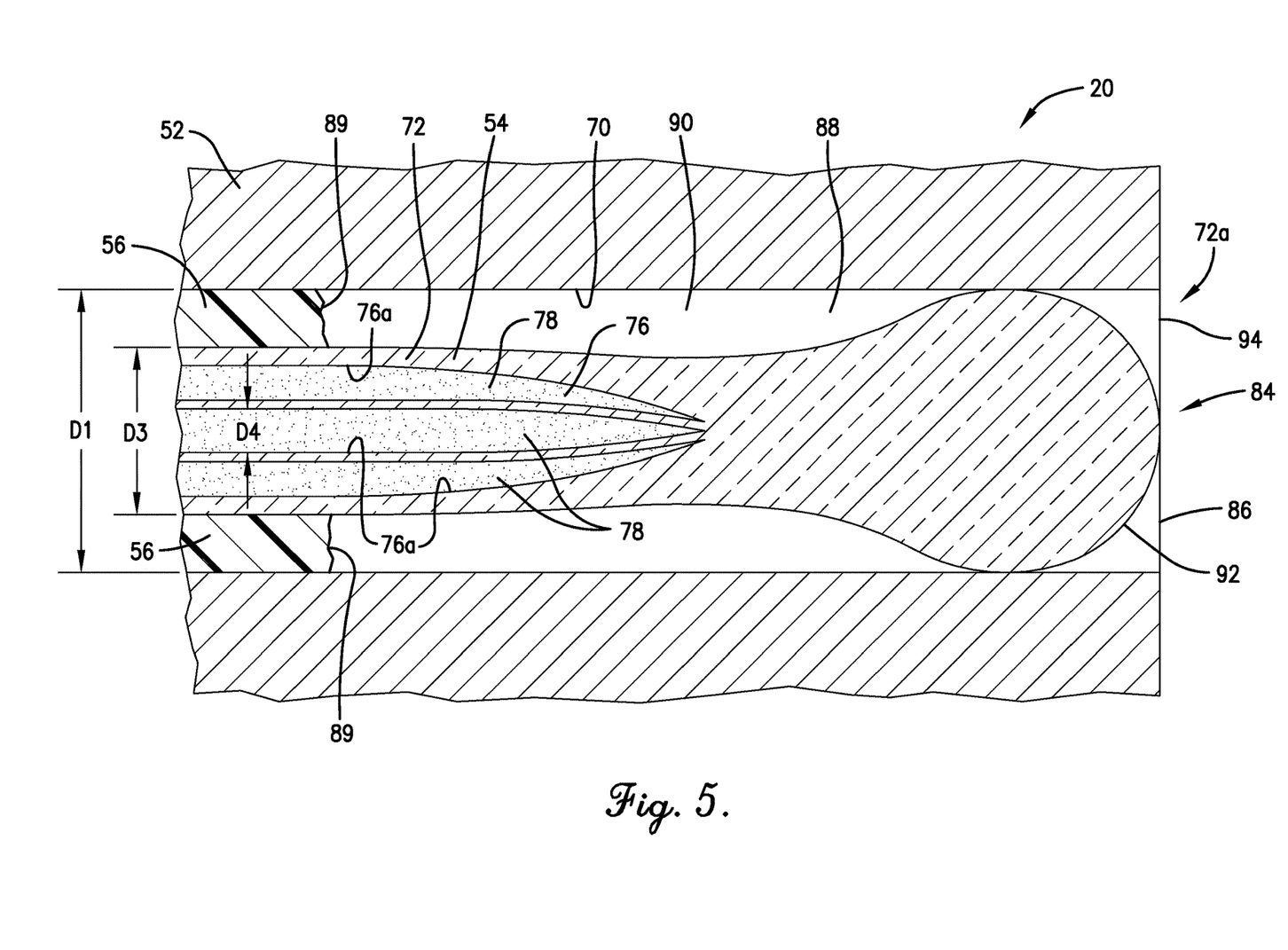
FIG. 5 is a fragmentary side elevation of the fluid-filled hollow optical fiber cell shown in FIGS. 1 and 4, showing the ferrule cross sectioned to depict the optical fiber assembly secured within the ferrule, with the optical fiber assembly including a rounded fiber end.

The ferrule 60 preferably presents a continuous bore 70 to receive the optical fiber assembly 54 (see FIG. 5). The bore 70 defines a bore diameter dimension D1 that preferably ranges from about one hundred fifty microns (150 μm) to about two hundred fifty microns (250 μm) and, more preferably, is about one hundred ninety microns (190 μm).

The ferrule 60 also presents a ferrule outer diameter dimension D2 (see FIG. 4) that preferably ranges from about one millimeter (1 mm) to about five millimeters (5 mm) and, more preferably, is about two and a half millimeters (2.5 μm).

The optical fiber assembly 54 preferably comprises a fluid-filled, hollow-core, photonic crystal fiber assembly. In the illustrated embodiment, the optical fiber assembly 54 includes a hollow-core, photonic crystal fiber 72 (also referred to as a "HC-PCF") and a solid core fiber 74 that are spliced to one another at a splice 75. The solid core fiber 74 preferably includes a single mode fiber, although an alternative solid core fiber could be used.

The hollow-core, photonic crystal fiber 72 is generally a microstructured fiber. The photonic crystal fiber 72 presents opposite ends 72a,b and a hollow core or passageway 76 that extends continuously between ends 72a,b of the fiber 72 (see FIGS. 3 and 5). The passageway 76 includes multiple passages 76a. As will be discussed, the passageway 76 is preferably configured to contain a volume of acetylene gas 78 (see FIG. 5).

The photonic crystal fiber 72 preferably presents a fiber outer diameter dimension D3 (see FIG. 5) that ranges from about one hundred microns (100 μm) to about one hundred fifty microns (150 μm) and, more preferably, is about one hundred twenty five microns (125 μm). However, the fiber outer diameter dimension D3 could fall outside of this range without departing from the scope of the present invention.

The photonic crystal fiber 72 preferably comprises a multiple cell photonic band gap (PBG) fiber that presents a core diameter dimension D4 (see FIG. 5). For instance, in one preferred embodiment, the fiber could include a 19 cell PBG fiber with a core diameter dimension of about twenty microns (20 μm). One such preferred PBG fiber is Model No. HC19-1550, supplied by NKT Photonics, although another suitable PBG optical fiber (such as another 19-cell PBG fiber) could be used.

In another preferred embodiment, the fiber could include a 7 cell PBG fiber with a core diameter dimension of about ten microns (10 μm). One such preferred PBG fiber is Model No. HC-1550, supplied by NKT Photonics, although another 7-cell PBG optical fiber could be used.

While the fiber 72 is preferably a photonic band gap fiber, it is within the scope of the present invention where the fiber 72 includes an alternative microstructured fiber. For instance, another hollow-core, photonic crystal fiber suitable for use with the present invention comprises a kagome fiber.

The optical fiber assembly 54 preferably includes acetylene gas 78 contained within the passageway 76. However, the optical fiber assembly 54 could contain an alternative reference gas. Yet further, for some aspects of the present invention, the fluid contained in the optical fiber assembly 54 could include at least some fluid in the form of a liquid (e.g., where the optical fiber assembly contains a gas, some of which is condensed into liquid form).

The optical fiber assembly 54 is preferably formed to hermetically seal acetylene gas 78 within the fiber 72. In particular, the photonic crystal fiber 72 is formed from an intermediate fiber 80 (see FIG. 2) to define fiber ends 72a,b that cooperatively provide the hermetic seal.

Initially, the second fiber end 72b is closed (see FIG. 2) before the first fiber end 72a is closed. The second fiber end 72b is preferably closed by positioning a fiber end of the solid core fiber 74 in abutting engagement with the second fiber end 72b and splicing the fiber ends to one another using a fusion splicing system S (see FIG. 2). With the second fiber end closed, the passageway 76 remains in fluid communication with ambient via an opening (not shown) at an opposite end of the intermediate fiber 80.

The splicing system S includes a laser L, an electric arc fusion splicer F, and a vacuum system V that presents a vacuum chamber C (see FIG. 2). Having closed the second fiber end 72b of the intermediate fiber 80, an open end 81 of the intermediate fiber 80 is inserted into the vacuum chamber C (see FIG. 2) so that the passageway 76 of the fiber 80 and the chamber C are in fluid communication. The fiber 80 is fluidly attached to the vacuum chamber C with a custom-made feedthrough (not shown) and evacuated for about twenty-four hours. The vacuum chamber C and the passageway 76 of the fiber 80 are then preferably filled with acetylene gas 78 to a predetermined absolute gas pressure. The gas pressure of the acetylene gas preferably ranges from about twenty (20) Torr to about five hundred (500) Torr, although the gas pressure could fall outside of this range.

While maintaining the gas pressure of the acetylene gas, the first fiber end 72a can then be formed by collapsing the intermediate fiber 80. More specifically, the intermediate fiber 80 is manually stripped and secured into fiber chucks of the fusion splicer F. The splicer F is preferably a Model No. FSU 995 FA, supplied by Ericsson. However, while an electric arc fusion splicer is preferably used to form the first fiber end 72a, a thermal fusion splicer could also be used.

The intermediate fiber 80 is positioned so that a second splice is initiated at a splice location 82 spaced from the second fiber end 72b (see FIG. 2). With the intermediate fiber 80 positioned for splicing, the splicer F is then operated so that the intermediate fiber 80 collapses and separates into two fiber pieces at the splice location 82. One of the two pieces includes the photonic crystal fiber 72, which is sealed by the splicing process to form the first fiber end 72a (see FIG. 3). In particular, the two pieces of the intermediate fiber 80 are drawn away from one another as the splice location is heated, with the two pieces being severed at the splice location 82.

The fusion splicer F is preferably programmed to heat the fiber 80 and to pull the two fiber pieces away from one another. The fusion splicer F preferably operates according to one of first and second programs P1,P2 when the ten micron (10 μm) fiber is being spliced (see Table 1 below). The fusion splicer F preferably operates according to a third program P3 when the twenty micron (20 μm) fiber is being spliced (see Table 1). However, it will be appreciated that the exact amount of current used to collapse the first fiber end 72a may vary depending on the gas pressure, due to changing thermal conductivity of the gas-filled region with changing pressure.

TABLE 1

|  | Program P1 10 μm fiber | Program P2 10 μm fiber | Program P3 20 μm fiber |
| --- | --- | --- | --- |
| Prefuse Time | 0.2 secs | 0.3 secs | 0.2 secs |
| Prefuse Current | 10.0 mA | 10.0 mA | 10.0 mA |
| Gap | 50.0 μm | 0.0 μm | 50.0 μm |
| Overlap | 10.0 μm | 0.0 μm | 10.0 μm |
| Fusion Time 1 | 0.3 secs | 9.0 secs | 0.3 secs |
| Fusion Current 1 | 12.7 mA | 15.5 mA | 13.0 mA |
| Fusion Time 2 | 2.0 secs | 7.0 secs | 2.0 secs |
| Fusion Current 2 | 19.9 mA | 13.5 mA | 20.0 mA |
| Fusion Time 3 | 2.0 secs | 2.0 secs | 2.0 secs |
| Fusion Current 3 | 15.1 mA | 7.0 mA | 12.5 mA |

The second fiber end 72b and the first fiber end 72a cooperatively define a length dimension D5 (see FIG. 3) that preferably ranges from about five centimeters (5 cm) to about nine centimeters (9 cm). However, for some aspects of the present invention, the length dimension could fall outside of the range.

As a result of the heating and severing process, the first fiber end 72a is formed into an enlarged rounded bulb, referred to as a "Q-tip" end shape. The first fiber end 72a presents a maximum end diameter dimension D6 (see FIG. 3) at a maximum diameter location 83 that ranges from about one hundred fifty microns (150 μm) to about two hundred microns (200 μm) and, more preferably, is about one hundred eighty microns (180 μm).

The maximum end diameter dimension D6 is preferably undersized relative to the bore diameter dimension D1 of the ferrule 60 (see FIG. 5). More specifically, the difference between the maximum end diameter dimension D6 and the bore diameter dimension D1 (D6-D1) preferably ranges from about five microns (5 µm) to about fifty microns (50 µm) and, more preferably, is about ten microns (10 µm).

As will be discussed, the optical fiber assembly 54 is preferably connectorized within the connector 52 to provide the optical fiber cell 20. However, for some aspects of the present invention the optical fiber assembly 54 could be used without a connector (such as the illustrated connector 52).

To connectorize the optical fiber assembly 54, the optical fiber assembly 54 is inserted into the boot 62 and the protective sleeve 64. In the depicted embodiment, the optical fiber assembly 54 is inserted so that the splice 75 is received and covered by both the protective sleeve 64 and the boot 62. Again, the protective sleeve 64 is partly received in the boot 62. As a result, the boot 62 and sleeve 64 each cover and extend on opposite sides of the splice 75. However, it is within the ambit of the present invention where the splice 75 is alternatively positioned. For example, if the photonic crystal fiber presents a longer length dimension D5, the splice could be located outside of the boot. In such an alternative embodiment, the sleeve preferably covers the splice 75. However, the sleeve may or may not be inserted within the boot.

It has been found that the illustrated optical fiber assembly 54 provides a reference cell with a line center uncertainty of about ten megahertz (10 MHz).

The optical fiber assembly 54 is preferably configured so that the first fiber end 72a is secured within the ferrule 60. Preferably, the first fiber end 72a is positioned so that an endmost margin 84 of the first fiber end 72a generally intersects an end opening 86 of the ferrule 60 when the first fiber end 72a is fixed to the ferrule 60 (see FIG. 5). The ferrule bore 70 and the optical fiber assembly 54 cooperatively define an annular space 88 therebetween (see FIG. 5). With the optical fiber assembly 54 located within the ferrule 60, the fiber 72 is preferably secured to the ferrule 60 with the cured epoxy 56.

Prior to using the epoxy 56, the optical fiber assembly 54 is positioned so that the first fiber end 72a protrudes from the end opening 86 a distance of about three millimeters (3 mm). With the first fiber end 72a protruding from the ferrule 60, the epoxy 56 is provided in liquid form and injected into the passageway 76 of the ferrule 60, at a location spaced from the end opening 86.

The first fiber end 72a can then be retracted into the ferrule 60 so that the first fiber end 72a generally intersects the end opening 86 of the ferrule 60. With the first fiber end 72a drawn into the ferrule 60, the epoxy 56 is located so that an endmost epoxy margin 89 is spaced from the end opening 86 and the annular space 88 is partly filled with the liquid epoxy 56 (see FIG. 5). That is, an unfilled portion 90 of the annular space 88 is preferably devoid of epoxy 56.

The maximum diameter location 83 of the first fiber end 72a is preferably spaced from the endmost epoxy margin 89. Also, an endmost surface 92 of the first fiber end 72a and an endmost portion 94 of the bore 70 are preferably devoid of epoxy 56 (see FIG. 5). That is, the endmost surface 92 and the endmost portion 94 are preferably not wetted with epoxy 56. More preferably, the entire bulb of the first fiber end 72a is devoid of epoxy 56 (see FIG. 5). With the epoxy 56 and fiber 72 positioned in the ferrule, the epoxy 56 is then permitted to cure into a solid form.

Because the endmost surface 92 of the first fiber end 72a and the space surrounded by endmost portion 94 of the bore 70 are preferably devoid of epoxy 56, the first fiber end 72a and the corresponding end of the ferrule 60 preferably require no polishing. That is, the connectorized first fiber end 72a are preferably coupled as part of the laser assembly 22 (or another system) without having to first polish the first fiber end 72a, the cured epoxy 56, or the ferrule 60.

The epoxy material preferably comprises epoxy Model No. F112, supplied by Thorlabs, Inc. However, an alternative adhesive could be used to fix the first fiber end 72a within the ferrule 60. After curing of the epoxy 56, the ferrule 60 and the first fiber end 72a are cleaned for attachment to other components (such as another fiber, another optical device, etc.).

In use, a ramp voltage is applied by the function generator 48 to operate the laser 24 through a range of laser frequencies. The ramp voltage of the function generator 48 is also provided to the oscilloscope 44. The oscilloscope 44 is used to compare the voltage output 50 of the function generator 48 with the output 42 of the photodetector 28.

Turning to FIGS. 6-9, an alternative optical fiber cell 200 is constructed in accordance with a second embodiment of the present invention. For the sake of brevity, the remaining description will focus primarily on the differences of this preferred embodiment from the preferred embodiment described above.

Figure 7:
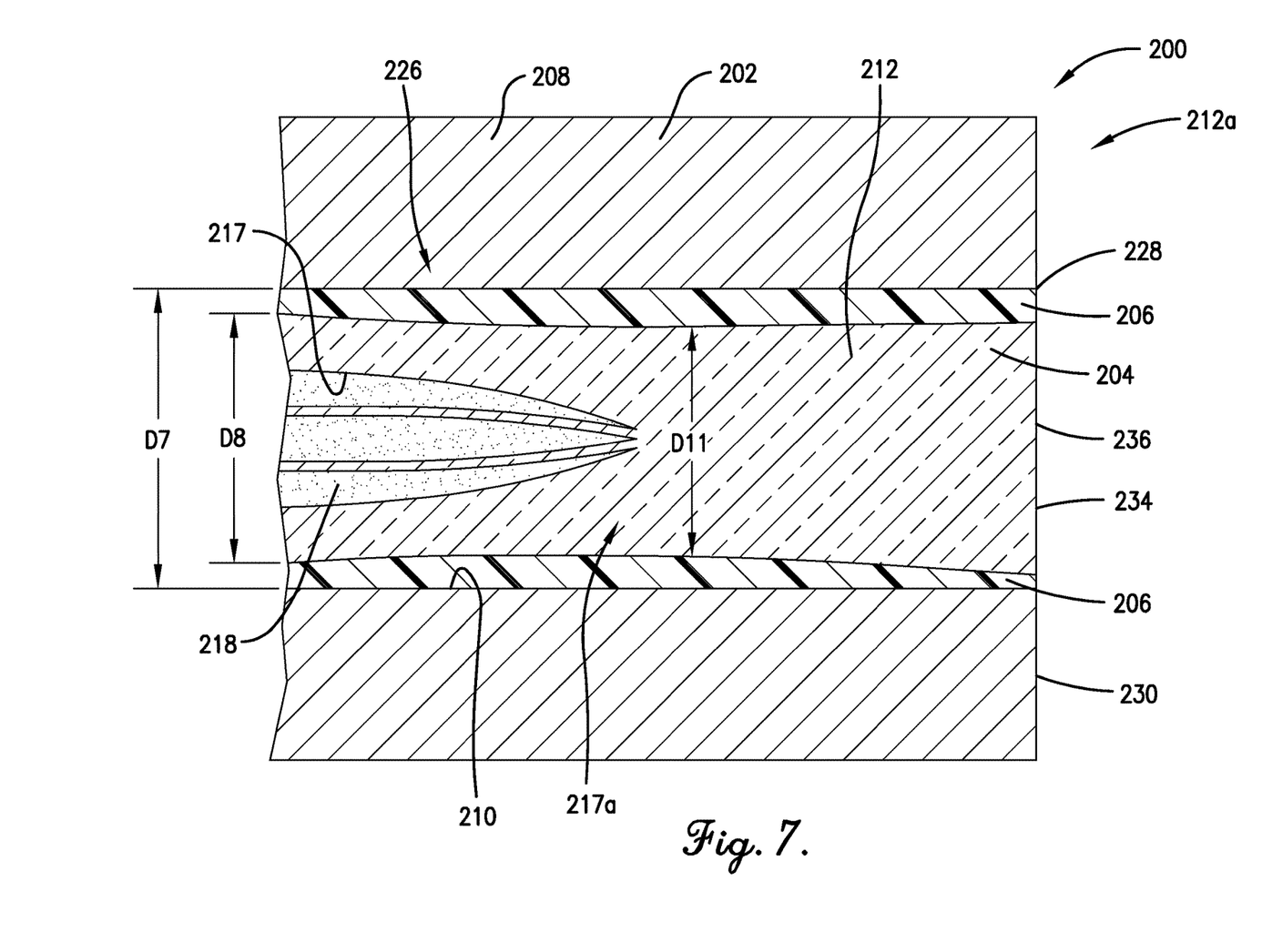
FIG. 7 is a fragmentary side elevation of the fluid-filled hollow optical fiber cell similar to FIG. 6, but showing the ferrule and the optical fiber assembly polished to form a polished end of the optical fiber cell.
Figure 8:
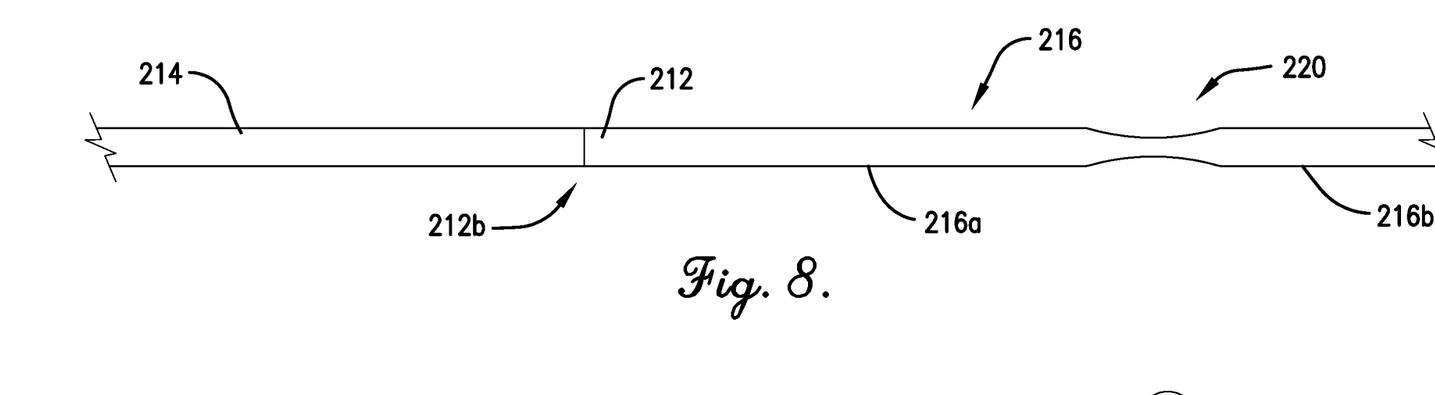
FIG. 8 is a fragmentary schematic view of a solid core fiber and an intermediate photonic crystal fiber that is used to form the optical fiber assembly shown in FIGS. 6 and 7, with the solid core fiber and intermediate fiber being joined at a splice to close an end of the intermediate fiber.
Figure 9:
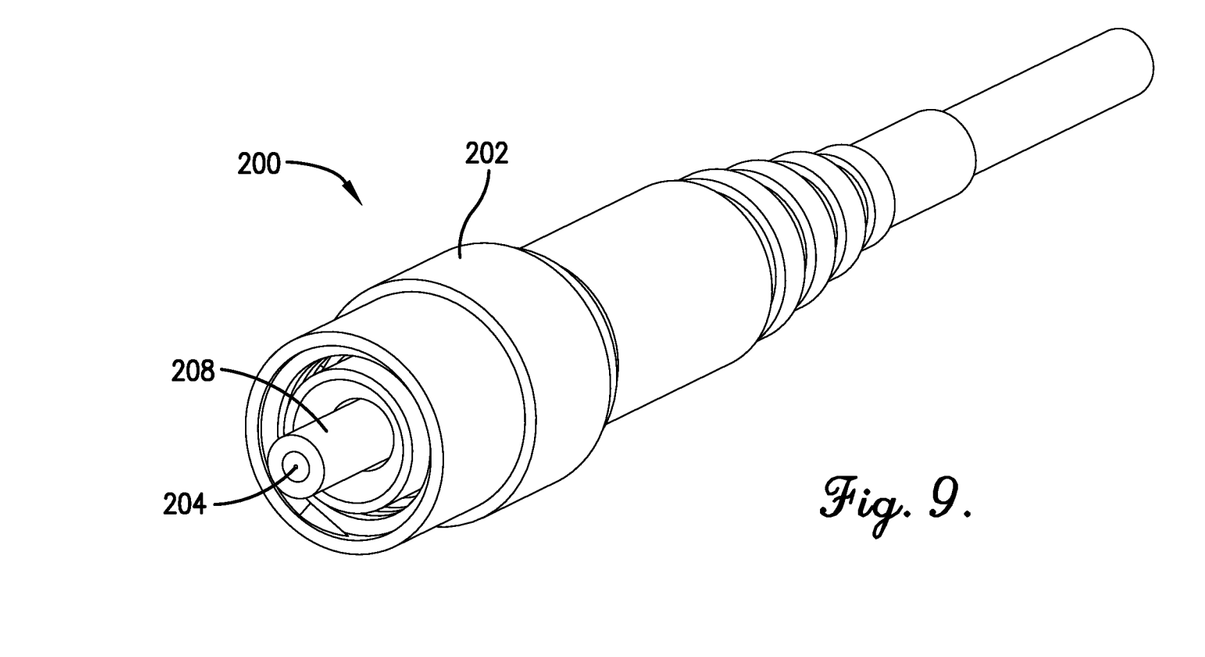
FIG. 9 is a fragmentary perspective view of the fluid-filled hollow optical fiber cell shown in FIGS. 6 and 7.

The optical fiber cell 200 preferably includes a connector 202 and a fluid-filled optical fiber assembly 204 mounted in the connector 202 with cured epoxy 206 (see FIGS. 7 and 9).

The illustrated connector 202 includes, among other things, an optical ferrule 208 (see FIGS. 7 and 9), which comprises an FC ceramic ferrule and preferably presents a continuous bore 210 to receive the optical fiber assembly 204. The bore 210 defines a bore diameter dimension D7 that preferably ranges from about fifty microns (50 µm) to about one hundred fifty microns (150 µm) and, more preferably, is about one hundred twenty-six microns (126 µm).

The illustrated optical fiber assembly 204 includes a hollow-core, photonic crystal fiber 212 and a solid core fiber 214. To construct the optical fiber assembly 204, the photonic crystal fiber 212 and solid core fiber 214 are spliced to one another to form an intermediate fiber 216 (see FIG. 8). The photonic crystal fiber 212 presents a first end 212a (see FIGS. 6 and 7), a second end 212b (see FIG. 8), and a hollow core or passageway 217 that extends continuously between the first end 212a and the second end 212b. The passageway 217 is preferably configured to contain a volume of acetylene gas 218.

The photonic crystal fiber 212 preferably presents a nominal fiber outer diameter dimension D8 (see FIG. 7) that ranges from about one hundred microns (100 µm) to about one hundred fifty microns (150 µm) and, more preferably, is about one hundred twenty five microns (125 µm). However, the fiber outer diameter dimension D8 could fall outside of this range without departing from the scope of the present invention.

The intermediate fiber 216 is secured in the fusion splicer F to form the fiber end 212a. In a tapering step, the fusion splicer F is programmed to heat the intermediate fiber 216 and pull two parts 216a,216b of the fiber 216 away from each other to form a tapered region 220 (see FIG. 8). During the tapering step, the fusion splicer F preferably performs the series of steps listed in program P4 (see Table 2 below) so that the fiber diameter in the tapered region 220 of the fiber 216 is reduced below the nominal fiber outer diameter D8 of the rest of the fiber 216. That is, the fiber diameter of the fiber 216 is tapered within the region 220.

After the tapering step, a collapsing step is performed by the fusion splicer F to collapse and seal the fiber end 212a. The fusion splicer F preferably operates according to program P5 (see Table 2 below) so that the fiber end 212a is collapsed to hermetically seal the acetylene gas 218 within the photonic crystal fiber 212. However, it will be appreciated that the exact amount of current used to collapse the first fiber end 212a may vary depending on the gas pressure, due to changing thermal conductivity of the gas-filled region with changing pressure.

TABLE 2

|  | Program P4<br>Tapering The Fiber | Program P5<br>Collapsing the Fiber End |
| --- | --- | --- |
| Fusion Time 1 | 15.0 secs | 5.0 secs |
| Fusion Current 1 | 12 mA | 12 mA |
| Fusion Time 2 | 5.0 secs | N/A |
| Fusion Current 2 | 10 mA | N/A |
| Fusion Time 3 | 10.0 secs | N/A |
| Fusion Current 3 | 7 mA | N/A |

Figure 6:
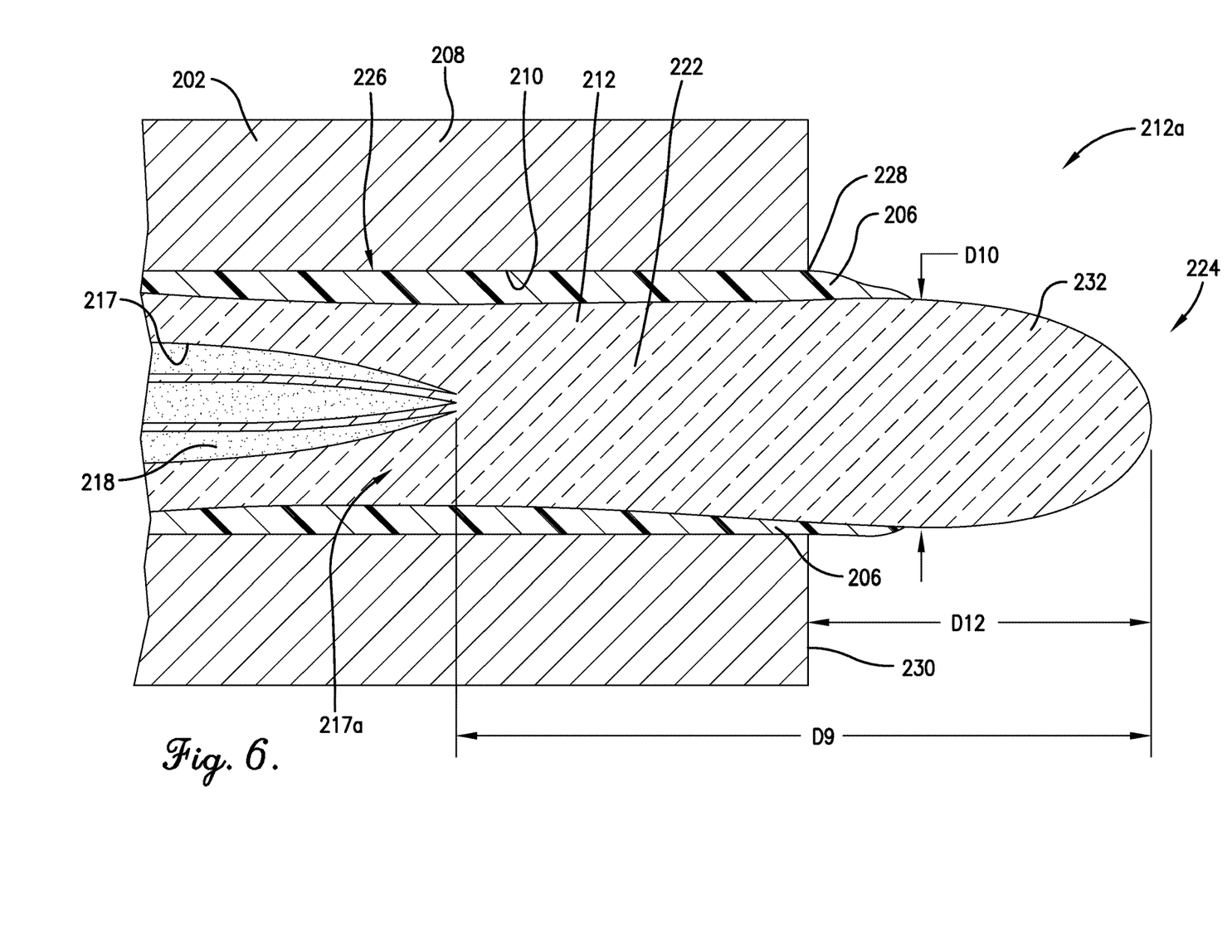
FIG. 6 is a fragmentary side elevation of a fluid-filled hollow optical fiber cell constructed in accordance with a second preferred embodiment of the present invention and showing a ferrule cross sectioned to depict an intermediate optical fiber assembly secured within the ferrule, with the optical fiber assembly including a rounded fiber end.

The tapering and collapsing steps used to form the fiber end 212a preferably form a solid end section 222 of the fiber end 212a (see FIG. 6). The depicted solid end section 222 terminates the passageway 217 and thereby hermetically seals the gas 218 within the fiber. The solid end section 222 defines an endmost fiber margin 224 and extends to a passageway end 217a, with the passageway end 217a being spaced from the endmost fiber margin 222 to define an intermediate solid length dimension D9 of the fiber 212 (see FIG. 6). The intermediate solid length dimension D9 preferably ranges from about fifty microns (50 µm) to about five hundred microns (500 µm) and, more preferably, is about three hundred microns (300 µm).

The tapering and collapsing steps also preferably produce a rounded end shape having a maximum end diameter dimension D10 that is about the same size as the nominal fiber outer diameter dimension (see FIG. 6). The maximum end diameter dimension D10 preferably ranges from about one hundred microns (100 µm) to about one hundred twenty-five microns (125 µm).

Due to the tapering process, it will be appreciated that the fiber 212 presents a reduced diameter region 226 adjacent the fiber end 212a. The illustrated reduced diameter region 226 presents a minimum diameter dimension D11 (see FIG. 7) less than the maximum end diameter dimension D10 and the nominal fiber outer diameter dimension D8.

The maximum end diameter dimension D10 is preferably undersized relative to the bore diameter dimension D7 of the ferrule 208 (see FIG. 7). More specifically, the difference between the maximum end diameter dimension D10 and the bore diameter dimension D7 preferably ranges from about one micron (1 µm) to about fifty microns (50 µm).

In the illustrated embodiment, the optical fiber assembly 204 is configured so that the fiber end 212a is secured and connectorized within the ferrule 208. Preferably, the first fiber end 212a is positioned so that the endmost margin 224 of the fiber end 212a projects beyond an end opening 228 of the ferrule 208 when the fiber end 212a is fixed to the ferrule 208 (see FIG. 6). With the optical fiber assembly 204 located within the ferrule 208, the fiber 212 is preferably secured to the ferrule 208 with the cured epoxy 206.

To connectorize the fiber end 212a, the epoxy 206 is injected into the bore 210 of the ferrule 208 using a syringe (not shown) so that a bead of epoxy is formed on a ferrule end 230. The fiber 212 is then moved into the bore 210 and through the ferrule 208 to a curing position (see FIG. 6) so that an exposed portion 232 of the fiber end 212a extends out of the ferrule 208. The epoxy 206 is permitted to cure while holding the fiber end 212a in the curing position.

The ferrule 208 and the fiber end 212a cooperatively define an exposed end length dimension D12 (see FIG. 6) associated with the exposed portion 232. The exposed end length dimension D12 is preferably less than the intermediate solid length dimension D9 to prevent the passageway 217 from being breached as a result of the connectorization process. Furthermore, the exposed end length dimension D12 preferably ranges from about fifty microns (50 µm) to about two hundred fifty microns (250 µm).

With the epoxy cured, connectorization of the fiber end 212a is completed by polishing the ferrule end 230 and the fiber end 212a to form a polished endface 234 of the optical fiber cell 200 (see FIG. 7). The endface 234 defines a polished endmost fiber margin 236 (see FIG. 7). In particular, the polished endface 234 is produced by removing the exposed portion 232 through a process of scribing the ferrule end 230 and the fiber end 212a and polishing the ferrule end 230 and the fiber end 212a with a conventional polishing film (not shown).

Although the above description presents features of preferred embodiments of the present invention, other preferred embodiments may also be created in keeping with the principles of the invention. Such other preferred embodiments may, for instance, be provided with features drawn from one or more of the embodiments described above. Yet further, such other preferred embodiments may include features from multiple embodiments described above, particularly where such features are compatible for use together despite having been presented independently as part of separate embodiments in the above description.

The preferred forms of the invention described above are to be used as illustration only, and should not be utilized in a limiting sense in interpreting the scope of the present invention. Obvious modifications to the exemplary embodiments, as hereinabove set forth, could be readily made by those skilled in the art without departing from the spirit of the present invention.

The inventors hereby state their intent to rely on the Doctrine of Equivalents to determine and assess the reasonably fair scope of the present invention as pertains to any apparatus not materially departing from but outside the literal scope of the invention as set forth in the following claims.

What is claimed is:

1. A fluid-filled hollow optical fiber cell comprising:
   a hollow-core optical fiber presenting first and second fiber ends and a longitudinal passageway that extends continuously between the fiber ends, the optical fiber having a nominal fiber outer diameter dimension; and
   a fluid occupying the passageway, with the fiber ends being closed to hermetically seal the fluid within the optical fiber,
   said first fiber end having a closed shape formed at least partly by melting the first fiber end to form melted fiber material, with the fiber material being permitted to solidify without splicing the first fiber end to another fiber so that the fiber material terminates the passageway at the first fiber end, said first fiber end having a maximum end diameter dimension,
   wherein the optical fiber comprises a tapered region wherein the fiber diameter dimension in the tapered region is reduced below the nominal fiber outer diameter dimension and the maximum end diameter dimension.

2. The fluid-filled hollow optical fiber cell as claimed in claim 1,
   said optical fiber comprising a photonic bandgap fiber.

3. The fluid-filled hollow optical fiber cell as claimed in claim 2,
said optical fiber being selected from the group consisting of a 19-cell PBG fiber and a 7-cell PBG fiber.

4. The fluid-filled hollow optical fiber cell as claimed in claim 1,
said optical fiber presenting a fiber length dimension that ranges from about five centimeters to about nine centimeters.

5. The fluid-filled hollow optical fiber cell as claimed in claim 1;
an optical ferrule presenting a bore that receives the first fiber end; and
adhesive located in the bore to adhere the fiber to the ferrule, with the fiber being at least partly wetted with adhesive.

6. The fluid-filled hollow optical fiber cell as claimed in claim 5; and
a solid-core fiber joined to the second fiber end at a splice.

7. The fluid-filled hollow optical fiber cell as claimed in claim 6; and
a protective sleeve covering the splice.

8. The fluid-filled hollow optical fiber cell as claimed in claim 5,
said adhesive comprising an epoxy material.

9. The fluid-filled hollow optical fiber cell as claimed in claim 5,
said bore and said optical fiber cooperatively defining an annular space therebetween,
said annular space being at least partly filled with adhesive.

10. The fluid-filled hollow optical fiber cell as claimed in claim 9,
said first fiber end including at least an endmost portion that is devoid of adhesive.

11. The fluid-filled hollow optical fiber cell as claimed in claim 1,
said fluid comprising acetylene gas.

12. The fluid-filled hollow optical fiber cell as claimed in claim 1,
said first fiber end being formed to present an endmost fiber margin and a passageway end spaced from the endmost fiber margin.

13. The fluid-filled hollow optical fiber cell as claimed in claim 12,
said first fiber end being polished to form a polished endface that defines the endmost fiber margin.

14. A method of making a fluid-filled hollow optical fiber cell comprising the steps of:

(a) introducing a fluid into the passageway of a hollow-core optical fiber having a nominal fiber outer diameter dimension, the hollow-core optical fiber having first and second fiber ends;

(b) heating a section of the hollow-core optical fiber intermediate the first and second fiber ends, and pulling the first and second fiber ends away from each other to form a tapered region having a fiber diameter dimension that is less than the nominal fiber outer diameter dimension; and (c) hermetically sealing the hollow-core optical fiber by closing the first and second fiber ends of the optical fiber to prevent the fluid in the passageway from flowing through the first and second fiber ends, step (c) including the steps of at least partly melting the first fiber end to form melted fiber material and permitting the melted fiber material to solidify without splicing the first fiber end to another fiber so that the fiber material terminates the passageway at the at first fiber end, the first fiber end having a maximum end diameter dimension that is greater than the fiber diameter dimension in the tapered region.

15. The method of making the fluid-filled hollow optical fiber cell as claimed in claim 14,
step (c) including the step of closing the second fiber end by splicing the second fiber end to the end of a solid core fiber.

16. The method of making the fluid-filled hollow optical fiber cell as claimed in claim 14; and
(d) adhering the first fiber end within the bore of an optical ferrule.

17. The method of making the fluid-filled hollow optical fiber cell as claimed in claim 16,
step (d) including the step of wetting at least part of the first fiber end with adhesive.

18. The method of making the fluid-filled hollow optical fiber cell as claimed in claim 17,
said step of wetting being performed so that at least an endmost portion of the first fiber end is devoid of adhesive.

19. The method of making the fluid-filled hollow optical fiber cell as claimed in claim 16; and
(e) polishing the first fiber end to form a polished endface that defines an endmost fiber margin,
step (c) including the step of closing the first fiber end to form a passageway end spaced from the endmost fiber margin.

* * * * *